(12) United States Patent
Tian et al.

(10) Patent No.: US 10,939,845 B2
(45) Date of Patent: Mar. 9, 2021

(54) FFL-BASED MAGNETIC PARTICLE IMAGING THREE-DIMENSIONAL RECONSTRUCTION METHOD, SYSTEM, AND DEVICE

(71) Applicant: INSTITUTE OF AUTOMATION, CHINESE ACADEMY OF SCIENCES, Beijing (CN)

(72) Inventors: Jie Tian, Beijing (CN); Peng Zhang, Beijing (CN); Hui Hui, Beijing (CN); Kun Wang, Beijing (CN); Xin Yang, Beijing (CN)

(73) Assignee: INSTITUTE OF AUTOMATION, CHINESE ACADEMY OF SCIENCES, Beijing (CN)

(*) Notice: Subject to any disclaimer, the term of this patent is extended or adjusted under 35 U.S.C. 154(b) by 0 days.

(21) Appl. No.: 16/907,334

(22) Filed: Jun. 22, 2020

(65) Prior Publication Data
US 2021/0015395 A1 Jan. 21, 2021

(30) Foreign Application Priority Data
Jul. 15, 2019 (CN) .......................... 201910637247.7

(51) Int. Cl.
*A61B 5/0515* (2021.01)
*A61B 5/00* (2006.01)

(52) U.S. Cl.
CPC .......... *A61B 5/0515* (2013.01); *A61B 5/7225* (2013.01)

(58) Field of Classification Search
CPC ........................... A61B 5/0515; A61B 5/7225
See application file for complete search history.

(56) References Cited

U.S. PATENT DOCUMENTS

| 9,301,693 B2* | 4/2016 | Liu | .......................... G06F 17/16 |
| 2009/0115415 A1* | 5/2009 | Weaver | ................ A61B 5/0515 |
| | | | 324/309 |

(Continued)

OTHER PUBLICATIONS

Iibey [Comparison of System-Matrix-Based and Projection-Based Reconstructions for Field Free Line Magnetic Particle Imaging International Journal on Magnetic Particle Imaging vol. 3, No. 1, Article ID 1703022, 8 Pages ] (Year: 2017).*

Goodwill ["Projection X-Space Magnetic Particle Imaging", IEEE Transactions on Medical Imaging, vol. 31, No. 5, May 2012] (Year: 2012).*

(Continued)

*Primary Examiner* — Oommen Jacob
(74) *Attorney, Agent, or Firm* — Bayramoglu Law Offices LLC

(57) ABSTRACT

A FFL-based magnetic particle imaging three-dimensional reconstruction method includes: acquiring current signal data of an induction coil during FFL-based three-dimensional scanning process of a scanned object; based on the current signal data, performing deconvolution through a preset kernel function to acquire a two-dimensional image data set, wherein the kernel function is a step function with L2 regularized constraint; based on the two-dimensional image data set, acquiring an initial three-dimensional image by using a Wiener filtering deconvolution algorithm; and based on the initial three-dimensional image, performing deconvolution through a Langevin function, and acquiring a final three-dimensional image by Radon transformation. A FFL-based magnetic particle imaging three-dimensional reconstruction system includes a magnet group, an induction coil, an imaging bed, and a control and imaging device, wherein, a magnetic particle imaging method in the control and imaging device is the FFL-based magnetic particle imaging three-dimensional reconstruction method.

12 Claims, 2 Drawing Sheets

(56) References Cited

U.S. PATENT DOCUMENTS

| | | | | |
|---|---|---|---|---|
| 2011/0221438 | A1* | 9/2011 | Goodwill | G01N 27/72 |
| | | | | 324/301 |
| 2012/0239341 | A1* | 9/2012 | Liu | A61B 5/01 |
| | | | | 702/130 |
| 2015/0015247 | A1* | 1/2015 | Goodwill | G01R 33/10 |
| | | | | 324/244 |
| 2015/0300987 | A1* | 10/2015 | Rahmer | A61B 5/0515 |
| | | | | 324/239 |
| 2016/0135710 | A1* | 5/2016 | Goodwill | A61B 5/0515 |
| | | | | 600/409 |
| 2018/0197278 | A1* | 7/2018 | Lee | G06K 9/4609 |
| 2018/0206757 | A1* | 7/2018 | Goodwill | A61B 5/0515 |
| 2018/0335487 | A1* | 11/2018 | Tonyushkin | G01R 33/10 |
| 2020/0245893 | A1* | 8/2020 | Goodwill | G01R 33/1276 |

OTHER PUBLICATIONS

Goodwill ["Multidimensional X-Space Magnetic Particle Imaging", IEEE Transactions on Medical Imaging, vol. 30, No. 9, Sep. 2011] (Year: 2011).*

Soulez ["A "Learn 2D, Apply 3D" Method for 3D Deconvolution Microscopy.", IEEE 2014] (Year: 2014).*

Bente ["Electronic Field Free Line Rotation and Relaxation Deconvolution in Magnetic Particle Imaging", IEEE Transactions on Medical Imaging, vol. 34, No. 2, Feb. 2015] (Year: 2015).*

Konkle ["Projection Reconstruction Magnetic Particle Imaging", IEEE Transactions on Medical Imaging, vol. 32, No. 2, Feb. 2013] (Year: 2013).*

Medimagh ["Artifacts in Field Free Line Magnetic Particle Imaging", IEEE 2015] (Year: 2015).*

* cited by examiner

FFL-BASED MAGNETIC PARTICLE IMAGING THREE-DIMENSIONAL RECONSTRUCTION METHOD, SYSTEM, AND DEVICE

CROSS REFERENCE TO THE RELATED APPLICATIONS

This application is based upon and claims priority to Chinese Patent Application No. 201910637247.7, filed on Jul. 15, 2019, the entire contents of which are incorporated herein by reference.

TECHNICAL FIELD

The present invention belongs to the field of magnetic particle imaging, and in particular relates to a FFL-based magnetic particle imaging three-dimensional reconstruction method, system, and device.

BACKGROUND

In clinical diagnosis and detection, how to accurately and objectively locate tumors and other lesions has been an international research hotspot and challenging issue. Existing medical imaging technologies such as computerized tomography (CT), magnetic resonance imaging (MRI), single photon emission computed tomography (SPECT) and other methods all have the problems of great harm, poor locating, and low accuracy. In recent years, a new tracer-based imaging method—magnetic particle imaging technology (MPI), has been proposed. By using tomographic imaging technology, MPI can detect the spatial concentration distribution of superparamagnetic iron oxide nanoparticles (SPIOs), which are harmless to the human body, so as to accurately locate tumors or targets. The MPI has the characteristics of three-dimensional imaging, high temporal-spatial resolution and high sensitivity. In addition, MPI does not show anatomical structures and is not subjected to background signal interference, and thus the strength of the detected signal is directly proportional to the concentration of the tracer. Therefore, MPI is a new method with considerable medical application potential.

Most of MPI systems in prior art are reconstructed on the basis of performing spatial encoding by constructing field free point (FFP). However, FFP has much lower spatial resolution and sensitivity than field free line (FFL). At present, the research of FFL-based magnetic particle imaging systems is still mainly focused on the acquisition of two-dimensional images, while the research on the acquisition of three-dimensional images based on FFL is less. Moreover, at present, the accuracy of the three-dimensional image of magnetic particle distribution acquired by the method of performing three-dimensional image reconstruction based on the electrical signal of the induction coil is relatively low.

SUMMARY

In order to solve the above problems in the prior art, namely, to solve the problem of low accuracy of FFL-based magnetic particle distribution three-dimensional images, the first aspect of the present invention proposes a FFL-based magnetic particle imaging three-dimensional reconstruction method, and the method includes the following steps:

step S100, acquiring current signal data of an induction coil during FFL-based three-dimensional scanning process of a scanned object;

step S200, based on the current signal data, performing deconvolution through a preset kernel function to acquire a two-dimensional image data set, wherein the kernel function is a step function with L2 regularized constraint;

step S300, based on the two-dimensional image data set, acquiring an initial three-dimensional image by using a Wiener filtering deconvolution algorithm; and step S400, based on the initial three-dimensional image, performing deconvolution through a Langevin function, and acquiring a final three-dimensional image by Radon transformation.

In some preferred embodiments, the step S100 of "acquiring the current signal data of the induction coil during the FFL-based three-dimensional scanning process of the scanned object" includes:

adopting a FFL-based magnetic particle imaging system to perform three-dimensional scanning on the scanned object by rotation and displacement of FFL;

and acquiring the current signal data of the induction coil in the magnetic particle imaging system during the scanning process.

In some preferred embodiments, before the step S200 of "performing deconvolution through the preset kernel function", the method further includes: performing analog-to-digital conversion on the current signal data.

The second aspect of the present invention proposes a FFL-based magnetic particle imaging three-dimensional reconstruction system, and the system includes a current signal data acquisition module, a two-dimensional image data set acquisition module, an initial three-dimensional image acquisition module and a final three-dimensional image acquisition module; wherein, the current signal data acquisition module is configured to acquire current signal data of an induction coil during FFL-based three-dimensional scanning process of a scanned object;

the two-dimensional image data set acquisition module is configured to perform deconvolution based on the current signal data through a preset kernel function to acquire a two-dimensional image data set, wherein the kernel function is a step function with L2 regularized constraint;

the initial three-dimensional image acquisition module is configured to acquire an initial three-dimensional image based on the two-dimensional image data set by using a Wiener filtering deconvolution algorithm; and the final three-dimensional image acquisition module is configured to perform deconvolution based on the initial three-dimensional image through a Langevin function and acquire a final three-dimensional image by Radon transformation.

The third aspect of the present invention proposes a FFL-based magnetic particle imaging three-dimensional reconstruction system, including a magnet group, an induction coil, an imaging bed, and a control and imaging device, wherein a magnetic particle imaging method in the control and imaging device is the FFL-based magnetic particle imaging three-dimensional reconstruction method described above.

The fourth aspect of the present invention proposes a storage device, wherein, the store device stores a plurality of programs, and the programs are configured to be loaded and executed by a processor to implement the FFL-based magnetic particle imaging three-dimensional reconstruction method described above.

The fifth aspect of the present invention proposes a processing device, including a processor and a store device, wherein, the processor is configured to execute a plurality of programs, the storage device is configured to store the plurality of programs, and the programs are configured to be loaded and executed by the processor to implement the FFL-based magnetic particle imaging three-dimensional reconstruction method described above.

The present invention has the following advantages.

In the present invention, for the current signal data acquired during the FFL-based three-dimensional scanning process of the scanned object, processing and transformation of data are performed in sequence through the constructed kernel function, the Wiener filtering deconvolution algorithm, the Langevin function and the Leiden transform, so as to acquire the final three-dimensional image, which improves the accuracy of locating the magnetic particles in the reconstructed three-dimensional image.

BRIEF DESCRIPTION OF THE DRAWINGS

Other features, objectives, and advantages of the present invention will become more apparent by reading a detailed description of non-restrictive embodiments made with reference to the following drawings.

DETAILED DESCRIPTION OF THE EMBODIMENTS

Figure 1:
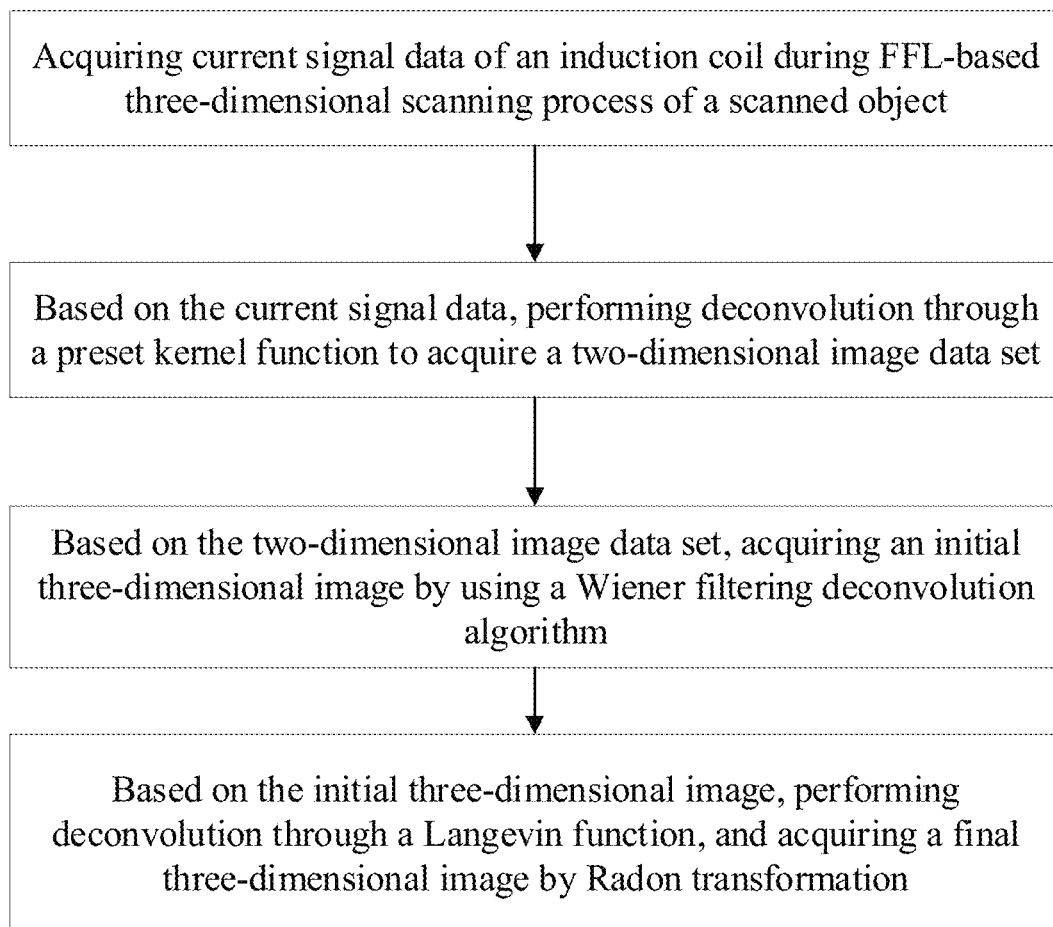
FIG. 1 is a schematic flowchart of a FFL-based magnetic particle imaging three-dimensional reconstruction method according to an embodiment of the present invention.

In order to make the objectives, technical solutions, and advantages of the present invention clearer, the technical solutions in the embodiments of the present invention will be clearly and completely described hereinafter with reference to the drawings. It is obvious that the described embodiments are a part of the embodiments of the present invention, but not all embodiments. All other embodiments acquired by those having ordinary skill in the art based on the embodiments of the present invention without creative efforts shall fall within the scope of protection of the present invention.

The present invention is further described below in detail in conjunction with the drawings and embodiments: It can be understood that the specific embodiments described herein are only used to explain the present invention, but not to limit the present invention. It should also be noted that, for ease of description, only the parts related to the present invention are shown in the drawings.

It should be noted that, in the case of no conflict, the embodiments in the present invention and the features in the embodiments can be combined with each other.

In the present invention, a current signal of an induction coil that changes with time in a FFL-based magnetic particle imaging system during three-dimensional scanning process of a scanned object is acquired through the FFL-based magnetic particle imaging system, and the current signal is used as the basis to perform magnetic particle imaging three-dimensional reconstruction.

A FFL-based magnetic particle imaging three-dimensional reconstruction method of the present invention includes the following steps.

Step S100: current signal data of an induction coil during FFL-based three-dimensional scanning process of a scanned object is acquired.

Step S200: based on the current signal data, deconvolution is performed through a preset kernel function to acquire a two-dimensional image data set, wherein the kernel function is a step function with L2 regularized constraint.

Step S300: based on the two-dimensional image data set, an initial three-dimensional image is acquired by using a Wiener filtering deconvolution algorithm.

Step S400: based on the initial three-dimensional image, deconvolution is performed through a Langevin function, and a final three-dimensional image is acquired by Radon transformation.

In order to more clearly explain the FFL-based magnetic particle imaging three-dimensional reconstruction method of the present invention, each step in an embodiment of the present invention is described below in detail in conjunction with the drawings.

As shown in FIG. 1, the FFL-based magnetic particle imaging three-dimensional reconstruction method according to an embodiment of the present invention includes the following steps.

Step S100, current signal data of an induction coil during FFL-based three-dimensional scanning process of a scanned object is acquired.

The current signal data is a current signal of the complete induction coil that changes with time during the three-dimensional scanning process of the scanned object. An acquisition method of the current signal data is as follows:

a FFL-based magnetic particle imaging system is adopted to perform three-dimensional scanning on the scanned object by rotation and translation of FFL; and the current signal data of the induction coil in the FFL-based magnetic particle imaging system during the scanning process is acquired.

Step S200, based on the current signal data, deconvolution is performed through a preset kernel function to acquire a two-dimensional image data set, wherein the kernel function is a step function with L2 regularized constraint.

In the step S200, before deconvolution is performed, it is also necessary to perform analog-to-digital conversion on the current signal data. Of course, the current signal data after the analog-to-digital conversion can also be directly acquired during the data acquisition in step S100 to reduce the calculation amount of the algorithm.

In the step S200, the two-dimensional image data set needs to be acquired through a point spread function (PSF) according to the current signal data, but it is impossible to find the true point spread function. Therefore, the two-dimensional image data set is usually acquired by using a approximate function of the point spread function. In the present embodiment, a step function with L2 regularized constraint is adopted as the approximate function, namely, the kernel function.

Step S300, based on the two-dimensional image data set, an initial three-dimensional image is acquired by using a Wiener filtering deconvolution algorithm.

The Wiener filtering deconvolution algorithm is a simple and practical super-resolution algorithm. Wiener filtering is a method of filtering noise mixed signals by using the correlated characteristic and spectral characteristic of a stationary random process. When the Wiener filtering is applied to the deconvolution problem, an optimal estimate of a true signal can be acquired under the minimum mean square error.

Step S400, based on the initial three-dimensional image, deconvolution is performed through a Langevin function, and a final three-dimensional image is acquired by Radon transformation.

The FFL-based magnetic particle imaging system used in an embodiment of the present invention includes a magnet group, an induction coil, an imaging bed, and a control and imaging device. Further, the magnetic particle imaging system of the present embodiment may further include an imaging bed moving device.

Figure 2:
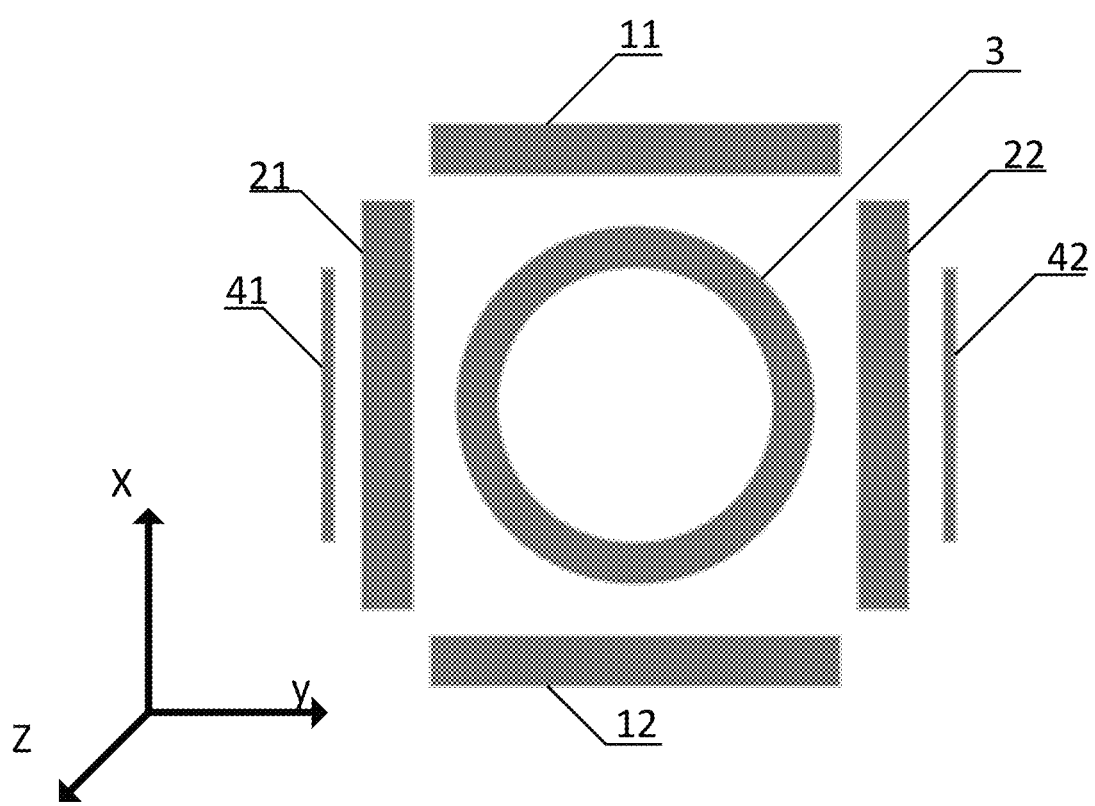
FIG. 2 is a schematic diagram of an arrangement structure of a magnet group and an induction coil in an FFL-based magnetic particle imaging system according to an embodiment of the present invention.

As shown in FIG. 2, the magnet group includes two pairs of ring magnets and one cylindrical magnet. The first ring magnet 11 and the second ring magnet 12 form a first magnet pair, the third ring magnet 21 and the fourth ring magnet 22 form a second magnet pair, and the cylindrical magnet 3 is arranged in the space surrounded by the first magnet pair and the second magnet pair. The first ring magnet 11 and the second ring magnet 12 are coaxially arranged in parallel, and the axis of the first ring magnet 11 and the second ring magnet 12 is defined as a first axis. Similarly, the third ring magnet 21 and the fourth ring magnet 22 are also coaxially arranged in parallel, and the axis of the third ring magnet 21 and the fourth ring magnet 22 is defined as a second axis. The first axis is orthogonal to the second axis. The axis of the cylindrical magnet 3 is defined as a third axis. The third axis passes through an orthogonal point of the first axis and the second axis, and the third axis is perpendicular to a plane (x-y plane) formed by the first axis and the second axis.

The control and imaging device is configured to control the magnetic field changes caused by the two pairs of ring magnets and the cylindrical magnet according to set control instructions, realizing the rotation and/or translation of the generated FFL to perform three-dimensional scanning on a scanned object arranged on the imaging bed. In the present embodiment, the rotation of FFL is rotation in the x-y plane to form a scanning surface based on the FFL, and the three-dimensional scanning is further realized based on the translation of the FFL in the z-axis.

Based on the first magnet pair, the second magnet pair and the cylindrical magnet 3, under the control of the control and imaging device, FFL is generated through two sets of orthogonal gradient magnetic fields, and the FFL is translated through an alternating magnetic field.

Continuously referring to FIG. 2, two induction coils (the first induction coil 41 and the second induction coil 42) are arranged outside the third ring magnet 21 and the fourth ring magnet 22 of the second magnet pair, respectively, so as to generate a corresponding induced current in real time based on the change of the magnetic field at a position where the two induction coils are located when the three-dimensional scanning of the scanned object is controlled by the rotation and translation of the FFL generated by the first magnet pair, the second magnet pair and the cylindrical magnet 3. In other embodiments, the induction coils may also be arranged outside the first ring magnet 11 and the second ring magnet 12 of the first magnet pair, respectively.

The induction coil is a toroidal induction coil, and the axis of the toroidal induction coil coincides with the axis of the second magnet pair.

The control and imaging device is further configured to perform magnetic particle imaging based on all current signals generated by the induction magnetic field in the induction coils during the three-dimensional scanning. There have been many descriptions of the imaging method in the prior art, which will not be repeated here. The control and imaging device can directly acquire the real-time electrical signal of the induction coils. Alternatively, the control and imaging device can acquire the complete signals of the entire process after the signal collection is completed, and in this case, however, a signal storage device of the induction coils is required to acquire and store the electrical signal of the induction coils in real time and transmit the electrical signal to the control and imaging device through a communication link.

The imaging bed has a half-cylindrical shape, and the bed body thereof is made of a fully transparent material, and the imaging bed is configured to fix the scanned object. The imaging bed is located in the cylindrical magnet 3 when the magnetic particle imaging system of the present embodiment scans the scanned object. Preferably, the center point of the imaging bed is located on the axis of the cylindrical magnet 3.

In order to better send the imaging bed to a target position, an imaging bed moving device is further provided. The imaging bed moving device includes a moving apparatus, a fixed bracket mounted on the moving apparatus, and a fixed sleeve mounted on the fixed bracket. The imaging bed is mounted in the fixed sleeve. The imaging bed can be moved to a set position in the cylindrical magnet by the moving apparatus. In order to better determine the position of the imaging bed, the axis of the fixed sleeve coincides with the axis of the cylindrical magnet 3 when the magnetic particle imaging system of the present embodiment scans the scanned object.

The moving apparatus is connected to the control and imaging device through the communication link, and is configured to receive and execute control instructions sent by the control and imaging device, so as to move the fixed sleeve. The moving apparatus of the present embodiment is a rail-type moving and positioning apparatus driven by a motor, or may also be a manually-controlled rail-type moving and positioning apparatus. In other embodiments, the moving apparatus may also be a robot arm or other structural members or devices that can move the fixed sleeve to the set position.

The two pairs of ring magnets and the cylindrical magnet are permanent magnets, or may also be electromagnetic coils. The permanent magnet is preferable in a small-scale MPI system. The permanent magnet has the following advantages: it is relatively small and easy to build without considering heat dissipation and power loss, is easy to generate a gradient magnetic field, and can significantly improve the performance of the scanner. The electromagnetic coil is preferable in a large-scale MPI imaging system. The electromagnetic coil is relatively flexible to control, and the size of the magnetic field can be changed according to the needs of the experiment. However, higher requirements for heat dissipation and voltage should be considered when the electromagnetic coil is adopted. When the electromagnetic coil is adopted, the two pairs of ring magnets may be Helmholtz coil pairs.

The control and imaging device is a computer.

A FFL-based magnetic particle imaging three-dimensional reconstruction system according to the second embodiment of the present invention is different from the above FFL-based magnetic particle imaging system in that the magnetic particle imaging method of the control and imaging device is replaced by the FFL-based magnetic particle imaging three-dimensional reconstruction method of the present invention.

A FFL-based magnetic particle imaging three-dimensional reconstruction system according to the third embodiment of the present invention includes a current signal data acquisition module, a two-dimensional image data set acquisition module, an initial three-dimensional image acquisition module, and a final three-dimensional image acquisition module.

The current signal data acquisition module is configured to acquire current signal data of an induction coil during FFL-based three-dimensional scanning process of a scanned object;

The two-dimensional image data set acquisition module is configured to perform deconvolution through a preset kernel function based on the current signal data to acquire a two-dimensional image data set, wherein the kernel function is a step function with L2 regularized constraint.

The initial three-dimensional image acquisition module is configured to acquire an initial three-dimensional image based on the two-dimensional image data set by using a Wiener filtering deconvolution algorithm.

The final three-dimensional image acquisition module is configured to perform deconvolution based on the initial three-dimensional image through a Langevin function and acquire a final three-dimensional image by Radon transformation.

It can be clearly understood by those skilled in the art that for the convenience and brevity of the description, reference may be made to the corresponding processes in the foregoing method embodiments for the specific working process and related description of the system described above, which will not be repeated here.

It should be noted that the FFL-based magnetic particle imaging three-dimensional reconstruction system provided in the above embodiments is only exemplified by the division of the above functional modules. In practical applications, the above functions may be allocated to be completed by different functional modules as needed, that is, the modules or steps in the embodiments of the present invention are further decomposed or combined. For example, the modules in the above embodiments can be merged into one module, or can be further split into a plurality of sub-modules to complete all or a part of the functions of the above description. The names of the modules and steps involved in the embodiments of the present invention are only to distinguish each module or step, and are not regarded as an improper limitation of the present invention.

A storage device according to the fourth embodiment of the present invention stores a plurality of programs therein, wherein the programs are configured to be loaded and executed by a processor to implement the FFL-based magnetic particle imaging three-dimensional reconstruction method described above.

A processing device according to the fifth embodiment of the present invention includes a processor and a storage device. The processor is configured to execute a plurality of programs, and the storage device is configured to store the plurality of programs. The programs are configured to be loaded and executed by the processor to implement the FFL-based magnetic particle imaging three-dimensional reconstruction method described above.

It can be clearly understood by those skilled in the art that for the convenience and brevity of the description, reference may be made to the corresponding processes in the foregoing method embodiments for the specific working process and related description of the storage device and the processing device described above, which will not be repeated here.

Those skilled in the art should be able to realize that the exemplary modules and method steps described in conjunction with the embodiments disclosed herein can be implemented by electronic hardware, computer software or a combination of the electronic hardware and the computer software. The programs corresponding to modules of software, steps of methods can be stored in a random access memory (RAM), a memory, a read-only memory (ROM), an electrically programmable ROM, an electrically erasable programmable ROM, a register, a hard disk, a removable disk, a compact disc-read only memory (CD-ROM), or any other form of storage medium well-known in the technical field. In order to clearly illustrate the interchangeability of electronic hardware and software, in the above description, the composition and steps of each embodiment have been generally described according to the functions. Whether these functions are performed by electronic hardware or software depends on specific applications and design constraints of the technical solution. Those skilled in the art may use different methods to implement the described functions for each specific application, but such implementation should not be considered to be beyond the scope of the present invention.

The terms "first", "second" and the like are used to distinguish similar objects, but not to describe or indicate a specific order or sequence.

The term "include/comprise" or any other similar terms are intended to cover non-exclusive inclusions, so that a process, method, article or apparatus/device including a series of elements not only includes those elements but also includes other elements that are not explicitly listed, or further includes elements inherent in the process, method, article or apparatus/device.

Hereto, the technical solutions of the present invention have been described in combination with the preferred implementations with reference to the drawings. However, it is easily understood by those skilled in the art that the scope of protection of the present invention is obviously not limited to these specific embodiments. Without departing from the principle of the present invention, those skilled in the art can make equivalent modifications or replacements to related technical features, and the technical solutions obtained through these modifications or replacements shall fall within the scope of protection of the present invention.

What is claimed is:

1. A FFL-based magnetic particle imaging three-dimensional reconstruction method, comprising the following steps:

step S100, acquiring current signal data of an induction coil during FFL-based three-dimensional scanning process of a scanned object;

step S200, based on the current signal data, performing deconvolution through a preset kernel function to acquire a two-dimensional image data set, wherein the preset kernel function is a step function with L2 regularized constraint that approximates a point spread function;

step S300, based on the two-dimensional image data set, acquiring an initial image by using a Wiener filtering deconvolution algorithm; and step S400, based on the initial image, performing deconvolution through a Langevin function, and acquiring a final three-dimensional image by Radon transformation; wherein the method is used in medical applications to accurately locate magnetic particles in the final three-dimensional image.

2. The FFL-based magnetic particle imaging three-dimensional reconstruction method of claim 1, wherein, the step S100 of acquiring the current signal data of the induction coil during the FFL-based three-dimensional scanning process of the scanned object comprises:

adopting a FFL-based magnetic particle imaging system to perform three-dimensional scanning on the scanned object by rotation and displacement of FFL; and acquiring the current signal data of the induction coil in the FFL-based magnetic particle imaging system during the FFL-based three-dimensional scanning process.

3. The FFL-based magnetic particle imaging three-dimensional reconstruction method of claim 1, wherein, before the step S200 of performing deconvolution through the preset kernel function, the FFL-based magnetic particle imaging three-dimensional reconstruction method further comprises: performing analog-to-digital conversion on the current signal data.

4. A FFL-based magnetic particle imaging three-dimensional reconstruction system, comprising a magnet group, an induction coil, an imaging bed, and a control and imaging device, wherein, a magnetic particle imaging method in the control and imaging device is the FFL-based magnetic particle imaging three-dimensional reconstruction method of claim 1.

5. A storage device, storing a plurality of programs, wherein, the plurality of programs are configured to be loaded and executed by a processor to implement the FFL-based magnetic particle imaging three-dimensional reconstruction method of claim 1.

6. A processing device, comprising a processor and a storage device, wherein, the processor is configured to execute a plurality of programs, the storage device is configured to store the plurality of programs, and the plurality of programs are configured to be loaded and executed by the processor to implement the FFL-based magnetic particle imaging three-dimensional reconstruction method of claim 1.

7. The FFL-based magnetic particle imaging three-dimensional reconstruction system of claim 4, wherein, the step S100 of acquiring the current signal data of the induction coil during the FFL-based three-dimensional scanning process of the scanned object comprises:

adopting a FFL-based magnetic particle imaging system to perform three-dimensional scanning on the scanned object by rotation and displacement of FFL; and acquiring the current signal data of the induction coil in the FFL-based magnetic particle imaging system during the FFL-based three-dimensional scanning process.

8. The FFL-based magnetic particle imaging three-dimensional reconstruction system of claim 4, wherein, before the step S200 of performing deconvolution through the preset kernel function, the FFL-based magnetic particle imaging three-dimensional reconstruction method further comprises: performing analog-to-digital conversion on the current signal data.

9. The storage device of claim 5, wherein, the step S100 of acquiring the current signal data of the induction coil during the FFL-based three-dimensional scanning process of the scanned object comprises:

adopting a FFL-based magnetic particle imaging system to perform three-dimensional scanning on the scanned object by rotation and displacement of FFL; and acquiring the current signal data of the induction coil in the FFL-based magnetic particle imaging system during the FFL-based three-dimensional scanning process.

10. The storage device of claim 5, wherein, before the step S200 of performing deconvolution through the preset kernel function, the FFL-based magnetic particle imaging three-dimensional reconstruction method further comprises: performing analog-to-digital conversion on the current signal data.

11. The processing device of claim 6, wherein, the step S100 of acquiring the current signal data of the induction coil during the FFL-based three-dimensional scanning process of the scanned object comprises:

adopting a FFL-based magnetic particle imaging system to perform three-dimensional scanning on the scanned object by rotation and displacement of FFL; and acquiring the current signal data of the induction coil in the FFL-based magnetic particle imaging system during the FFL-based three-dimensional scanning process.

12. The processing device of claim 6, wherein, before the step S200 of performing deconvolution through the preset kernel function, the FFL-based magnetic particle imaging three-dimensional reconstruction method further comprises: performing analog-to-digital conversion on the current signal data.

* * * * *